United States Patent
Scaife et al.

(10) Patent No.: US 6,407,128 B1
(45) Date of Patent: Jun. 18, 2002

(54) METHOD FOR INCREASING THE BIOAVAILABILITY OF METAXALONE

(75) Inventors: Michael Scaife, Poway; Jaymin Shah, Sunnyvale, both of CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/998,206

(22) Filed: Dec. 3, 2001

(51) Int. Cl.⁷ .............................................. A61K 31/42
(52) U.S. Cl. ....................................................... 514/376
(58) Field of Search ......................................... 514/376

(56) References Cited

U.S. PATENT DOCUMENTS

| | | | |
|---|---|---|---|
| 3,062,827 A | * 11/1962 | Lunsford | .................... 260/307 |
| 3,993,767 A | 11/1976 | Alphin et al. | |
| 4,036,957 A | 7/1977 | Alphin et al. | |
| 4,058,621 A | 11/1977 | Hill | |
| 4,208,405 A | 6/1980 | Fouad | |
| 4,784,852 A | 11/1988 | Johansson | |
| 4,792,449 A | 12/1988 | Ausman et al. | |
| 4,820,690 A | 4/1989 | Gregory et al. | |
| 5,785,976 A | 7/1998 | Westesen et al. | |
| 5,840,688 A | 11/1998 | Tso | |
| 5,977,175 A | 11/1999 | Lin | |
| 5,989,583 A | 11/1999 | Amselem | |
| 6,030,988 A | 2/2000 | Gilis et al. | |
| 6,099,859 A | 8/2000 | Cheng et al. | |
| 6,103,269 A | 8/2000 | Wunderlich et al. | |
| 6,114,379 A | 9/2000 | Wheelwright et al. | |
| 6,143,325 A | 11/2000 | Dennis et al. | |
| 6,197,757 B1 | 3/2001 | Perrier et al. | |
| 6,207,178 B1 | 3/2001 | Westesen et al. | |
| 6,265,438 B1 | 7/2001 | Steward | |
| 2001/0024659 A1 | 9/2001 | Chen et al. | |

OTHER PUBLICATIONS

Monograph No. 5838 of the Merck Index (11$^{th}$ ed., 1989) for metaxalone.
Lunsford et al., 82 J. Am. Chem. Soc. 1166 (1960).
Skelaxin® monograph, 2001 Physicians' Desk Reference.

* cited by examiner

*Primary Examiner*—Raymond Henley, III
(74) *Attorney, Agent, or Firm*—Finnegan, Henderson, Farabow, Garrett & Dunner

(57) ABSTRACT

A method of increasing the bioavailability of metaxalone by administration of an oral dosage form with food is provided, as well as an article of manufacture comprising an oral dosage form of metaxalone in a suitable container and associated with printed labeling which describes the increased bioavailability of the medication in the container when taken with food.

22 Claims, 1 Drawing Sheet

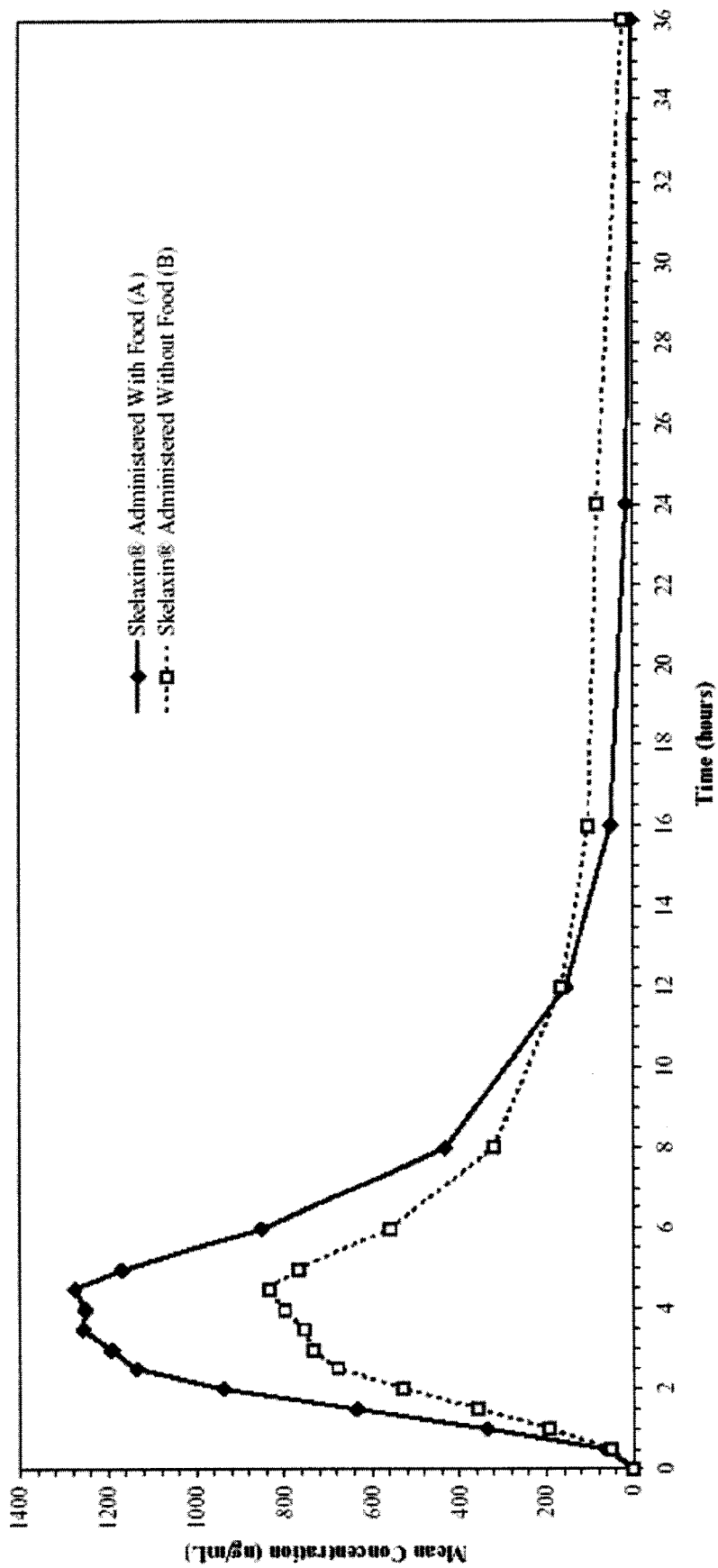
Figure I
Mean Plasma Concentration (0-36 hours)
Number =42

METHOD FOR INCREASING THE BIOAVAILABILITY OF METAXALONE

FIELD OF THE INVENTION

The invention relates to methods for increasing the bioavailability of a medicinal agent, namely metaxalone (5-[(3, 5-dimethylphenoxy)methyl]-2 oxazolidinone).

BACKGROUND OF THE INVENTION

Metaxalone (Skelaxin®) has the following chemical structure and name:

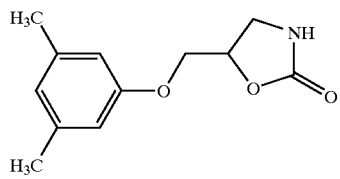

5-[(3,5 -dimethylphenoxy)methyl]-2 oxazolidinone

Skelaxin is indicated as an adjunct to rest, physical therapy, and other measures for the relief of discomforts associated with acute, painful musculoskeletal conditions. The mode of action of this drug has not been clearly identified, but may be related to its sedative properties. Metaxalone does not directly relax tense skeletal muscles in man. The commercially available tablet contains: metaxalone, 400 mg along with inert compression tableting excipients.

Metaxalone is further described at Monograph no. 5838 of the Merck Index (Eleventh Addition, Merck & Co., 1989) and is also identified by CAS Registry Number: 1665–48-1. It is also known by the drug code, AHR-438; and the drug product containing it is marketed as Skelaxin® (a trademark of Elan Pharmaceuticals, Inc.).

Preparation of metaxalone is described in Lunsford et al., J. Am. Chem. Soc. 82, 1166 (1960) and U.S. Pat. No. 3,062,827 to Lunsford Nov. 6, 1962 Assignee A. H. Robins), which is incorporated herein in its entirety by reference. The '827 patent discloses the compound and related species as anticonvulsants and antispasmodics, however, these activities have not been borne out by clinical experience.

Metaxalone is a central nervous system depressant that has sedative and skeletal muscle relaxant effects. Metaxalone is indicated as an adjunct to rest, physical therapy and other measures for the relief of discomforts associated with acute, painful muscoloskeletal conditions. See Skelaxin® monograph, 2001 Physicians' Desk Reference®, Medical Economics Company, Inc. (publisher) Montvale, N.J.

The most frequent reactions to metaxalone include nausea, vomiting, gastrointestinal upset, drowsiness, dizziness, headache, and nervousness or "irritability." Other adverse reactions are: hypersensitivity reaction, characterized by a light rash with or without pruritus; leukopenia; hemolytic anemia; jaundice.

Pharmacokinetic studies have not previously been conducted to date to evaluate the effect of food on the pharmacokinetics of metaxalone. The hydrophobicity of the metaxalone molecule and the dosage amount required for a therapeutic effect both point to probably limited absorption from the gut when administered orally. More oral bioavailability of the drug substance has been sought to increase both speed of onset and amount of therapeutic effect.

BRIEF DESCRIPTION OF THE DRAWINGS

FIG. 1 is a plot of the mean plasma concentration of metaxalone in nanograms per milliliter versus the time elapsed from administration of the dosage form. Two (2) plots are shown for the 400 mg dosage form administered with and without food.

SUMMARY OF THE INVENTION

The subject of this invention is the unexpected finding that administration of metaxalone with food increases both the rate and extent of absorption via the oral dosage form in human subjects.

One aspect of this invention is a method of increasing the bioavailability of metaxalone in a human patient receiving metaxalone therapy wherein the metaxalone is contained in a pharmaceutical composition, which method comprises administering a therapeutically effective amount of metaxalone to the patient with food.

Another aspect of the invention is providing a method of increasing rate and extent of metaxalone absorption as measured by the drug concentration attained in the blood stream over time of a patient receiving, the drug in an oral dosage form which method comprises administering a therapeutically effective amount of metaxalone to the patient with food.

Preferably the therapeutic amount is between about 200 mg to about 900 mg, and more preferably between about 400 mg to about 800 mg. Unit dosage forms are preferred.

Preferably the food is a solid food with sufficient bulk and fat content that it is not rapidly dissolved and absorbed in the stomach. More preferably the food is a meal, such as breakfast, lunch or dinner. Advantageously the dosage is administered to the patient between about 30 minutes prior to about 2 hours after eating a meal, most advantageously the dosage is administered within 15 minutes of eating a meal. The terms "without food", "fasted" and "an empty stomach" are defined to mean the condition of not having consumed solid food for about 1 hour prior to until about 2 hours after such consumption.

Yet another aspect of this invention is providing information to prescribing physicians and patients receiving metaxalone therapy useful in maximizing the therapeutic effect of the oral dosage form, by recommending that metaxalone be taken within about half an hour of consuming food.

Another aspect of this invention is an article of manufacture that comprises a container containing a pharmaceutical composition comprising metaxalone wherein the container holds preferably the metaxalone composition in unit dosage form and is associated with printed labeling instructions advising of the differing absorption when the pharmaceutical composition is taken with and without food.

The effect of food on metaxalone absortpion was identified in a study designed to compare the bioavailability of 400 mg of metaxalone in the formulation the drug product Skelaxin® administered to healthy volunteers with and without food.

An objective was to evaluate the bioavailability of metaxalone when administered to subjects with and without food. A single center, single dose, open-label, two-period, randomized, crossover trial in healthy subjects was conducted over a period of approximately 32 days.

The two study drug treatments were as follows:
Treatment A: metaxalone tablet (400 mg) administered with food
Treatment B: metaxalone tablet (400 mg) administered without food In fed treatment condition A, study drug was taken 15 minutes after th e test meal. The test meal was consumed over a 15 minute time period. There was a 6-day washout period between study drug administrations. Seventeen blood samples were collected, starting with baseline (0 hour) and at the following time points: 0.5, 1, 1.5, 2, 2.5, 3, 3.5, 4, 4.5, 5, 6, 8, 12, 16, 24, and 36 hours.

A total of 44 subjects (31 males/13 females) were enrolled and dosed. Only the plasma of subjects who completed the study were assayed and used for the pharmacokinetic analysis.

A single center, single dose, open label, two-period crossover trial was devised for study in healthy subjects. Each administration was a single oral dose of one Skelaxin® 400 mg tablet with or without food. The study drug was administered as follows:

Treatment A: One (1) 400 mg tablet of metaxalone with 240 mL of room temperature water with food: Breakfast was given to the subjects 30 minutes prior to dosing and eaten within a 15 minute period. The dose of study drug was administered to the subjects 15 minutes after the breakfast was finished.

The breakfast consisted of the following:
2 eggs (fried in butter);
2 strips of bacon;
2 slices of toast with butter;
4 ounces of hash brown potatoes;
1 glass whole milk (8 ounces).

Treatment B: 1 tablet of metaxalone with 240 mL of room temperature water without food. The study drug was administered with 240 mL room temperature water. A mouth check was performed to verify that the subjects swallowed the dose. Subjects were sequentially dosed at 1 minute intervals. The actual time of dosing was recorded on the Master Flow Sheet (refer to the Appendix 16.3.2 Clinical Study Data). Drug administration (1×400 mg capsule) was assisted with 240 mL of room temperature water consumed under direct observation. Immediately after administration of product, the subject's oral cavity was checked to confirm complete medication and fluid consumption. Dosing was completed as scheduled in 42 of 44 subjects.

The drug substance, metaxalone; was dosed in tablet form. Content: 400 mg; Route: Oral, Batch/Lot No.: SKLWW263F; Expiration Date: FEB03; Manufacturer: West-Ward Pharmaceutical Corp All pharmacokinetic parameters were analyzed by non-compartmental methods. The following PK parameters were calculated for the two PK profiles and are defined as follows:

Tmax: Time to maximum concentration;

Cmax: Observed maximum concentration;

kel: Slope of terminal linear portion of concentration/time curve;

T½: Half-life of metaxalone calculated as: 0.693/Kel;

AUC(last): Area under the curve to last quantifiable concentration as measured by the trapezoidal rule;

AUC(inf): The AUC value extrapolated to infinity calculated as: AUC(inf)=AUC(last)+C(t)last/Kel where C(t) last is the last measurable concentration.

Statistical Analysis

All statistical analyses were performed using SAS® software version 6.08 or higher. The PK parameters between the two treatments were compared using an appropriate ANOVA model (analysis of variance) that includes term for treatment, sequence, and period effect. Ninety percent confidence interval was computed for the Cmax and AUC values of the fed treatment with fasting as the reference treatment. During the study there were no protocol deviations to confound the pharmacokinetic and bioavailability analyses. Study results were not corrected for drug potency. The individual test results are summarized in table I

TABLE I

Summary of AUC$_{inf}$ and Ln-Transformed AUC$_{inf}$ for
Skelaxin ® Administered With Food (A) vs. Skelaxin ® Administered Without Food (B)

| Subj | Seq. | A: With Food (ng/mL) | B: Without Food (ng/mL) | (A − B) | Ratio (A/B) | % Ratio (A/B) *100 | Log$_e$ A Ln(A) | Log$_e$ B Ln(B) | Log$_e$ Ratio Ln (Ratio) |
|---|---|---|---|---|---|---|---|---|---|
| 2 | 1 | 9031 | 9855 | 824 | 0.916 | 91.64 | 9.108 | 9.196 | 0.087 |
| 3 | 2 | 9609 | 13103 | 3494 | 0.733 | 73.33 | 9.170 | 9.481 | 0.310 |
| 4 | 2 | 5011 | 3867 | 1144 | 1.296 | 129.58 | 8.519 | 8.260 | 0.259 |
| 5 | 1 | 3389 | 2530 | 859 | 1.340 | 133.95 | 8.128 | 7.836 | 0.292 |
| 6 | 2 | 10456 | 7302 | 3154 | 1.432 | 143.19 | 9.255 | 8.896 | 0.359 |
| 7 | 2 | 11217 | 11103 | 114 | 1.010 | 101.03 | 9.325 | 9.315 | 0.010 |
| 8 | 2 | 4025 | 3857 | 168 | 1.044 | 104.36 | 8.300 | 8.258 | 0.043 |
| 9 | 2 | 13708 | 8876 | 4832 | 1.544 | 154.44 | 9.526 | 9.091 | 0.435 |
| 11 | 2 | 8122 | 6570 | 1552 | 1.236 | 123.62 | 9.002 | 8.790 | 0.212 |
| 12 | 1 | 6739 | 5470 | 1269 | 1.232 | 123.20 | 8.816 | 8.607 | 0.209 |
| 13 | 2 | 4614 | 4360 | 254 | 1.058 | 105.83 | 8.437 | 8.380 | 0.057 |
| 14 | 1 | 17347 | 13467 | 3880 | 1.288 | 128.81 | 9.761 | 9.508 | 0.253 |
| 15 | 2 | 5488 | 3535 | 1953 | 1.552 | 155.25 | 8.610 | 8.170 | 0.440 |
| 16 | 1 | 12327 | 12025 | 302 | 1.025 | 102.51 | 9.420 | 9.395 | 0.025 |
| 17 | 1 | 4070 | 3320 | 750 | 1.226 | 122.59 | 8.311 | 8.108 | 0.204 |
| 18 | 1 | 5296 | 4365 | 931 | 1.213 | 121.33 | 8.575 | 8.381 | 0.193 |
| 19 | 2 | 8022 | 8271 | 249 | 0.970 | 96.99 | 8.990 | 9.021 | 0.031 |
| 20 | 2 | 2962 | 2874 | 88 | 1.031 | 103.06 | 7.994 | 7.963 | 0.030 |
| 21 | 1 | 9143 | 7173 | 1970 | 1.275 | 127.46 | 9.121 | 8.878 | 0.243 |
| 22 | 2 | 11873 | 7742 | 4131 | 1.534 | 153.36 | 9.382 | 8.954 | 0.428 |
| 23 | 1 | 10456 | 9983 | 473 | 1.047 | 104.74 | 9.255 | 9.209 | 0.046 |
| 24 | 1 | 6507 | 5529 | 978 | 1.177 | 117.69 | 8.781 | 8.618 | 0.163 |
| 25 | 2 | 12143 | 10272 | 1871 | 1.182 | 118.21 | 9.405 | 9.237 | 0.167 |
| 26 | 1 | 4519 | 5391 | 872 | 0.838 | 83.82 | 8.416 | 8.592 | 0.176 |

TABLE I-continued

Summary of AUC$_{inf}$ and Ln-Transformed AUC$_{inf}$ for
Skelaxin ® Administered With Food (A) vs. Skelaxin ® Administered Without Food (B)

| Subj | Seq. | A: With Food (ng/mL) | B: Without Food (ng/mL) | (A − B) | Ratio (A/B) | % Ratio (A/B) *100 | Log$_e$ A Ln(A) | Log$_e$ B Ln(B) | Log$_e$ Ratio Ln (Ratio) |
|---|---|---|---|---|---|---|---|---|---|
| 27 | 1 | 5208 | 5061 | 147 | 1.029 | 102.90 | 8.558 | 8.529 | 0.029 |
| 28 | 2 | 5197 | 5012 | 185 | 1.037 | 103.69 | 8.556 | 8.520 | 0.036 |
| 29 | 1 | 10355 | 11601 | 1246 | 0.893 | 89.26 | 9.245 | 9.359 | 0.114 |
| 30 | 1 | 7350 | 6452 | 898 | 1.139 | 113.92 | 8.902 | 8.772 | 0.130 |
| 31 | 1 | 7899 | 7677 | 222 | 1.029 | 102.89 | 8.974 | 8.946 | 0.029 |
| 32 | 2 | 6719 | 4440 | 2279 | 1.513 | 151.33 | 8.813 | 8.398 | 0.414 |
| 33 | 2 | 11295 | 11316 | 21 | 0.998 | 99.81 | 9.332 | 9.334 | 0.002 |
| 34 | 2 | 13357 | 13580 | 223 | 0.984 | 98.36 | 9.500 | 9.516 | 0.017 |
| 35 | 2 | 10710 | 10138 | 572 | 1.056 | 105.64 | 9.279 | 9.224 | 0.055 |
| 36 | 1 | 19077 | 19329 | 252 | 0.987 | 98.70 | 9.856 | 9.869 | 0.013 |
| 37 | 1 | 6727 | 4454 | 2273 | 1.510 | 151.03 | 8.814 | 8.402 | 0.412 |
| 38 | 2 | 19024 | 9934 | 9090 | 1.915 | 191.50 | 9.853 | 9.204 | 0.650 |
| 39 | 1 | 3060 | 3284 | 224 | 0.932 | 93.18 | 8.026 | 8.097 | 0.071 |
| 40 | 1 | 5188 | 4203 | 985 | 1.234 | 123.44 | 8.554 | 8.344 | 0.211 |
| 41 | 1 | 7273 | 6574 | 699 | 1.106 | 110.63 | 8.892 | 8.791 | 0.101 |
| 42 | 2 | 3958 | 3642 | 316 | 1.087 | 108.68 | 8.283 | 8.200 | 0.083 |
| 43 | 1 | 8837 | 4642 | 4195 | 1.904 | 190.37 | 9.087 | 8.443 | 0.644 |
| 44 | 2 | 11427 | 11935 | 508 | 0.957 | 95.74 | 9.344 | 9.387 | 0.043 |

Differences were declared to be significant at the 5% level. The ratio of the geometric means for the ln-transformed data and the corresponding 90% confidence intervals were calculated for AUC(last), AUC(inf), and Cmax. The calculations for the confidence intervals used the least squares means (LSMEANS) and the standard error of the estimate, both generated by the SAS® software.

The lower limit of quantitation for metaxalone was 10 ng/mL. For statistical analysis, subject sample values below the lower limit of quantitation were reported as zero.

Tables IIa and IIb summarize the results of the analyses performed on the pharmacokinetic parameters obtained from the fed and fasted states.

TABLE IIa

| Metaxalone | Ln-Transformed AUC(last) | Ln-Transformed AUCinf | Ln-Transformed Cmax |
|---|---|---|---|
| Treatment A Geometric Mean | 7525.00 | 7630.53 | 1536.23 |
| Treatment B Geometric Mean | 6094.12 | 6615.24 | 865.34 |
| % Ratio | 123.48 | 115.35 | 177.53 |
| 90% Confidence Interval | (116.40, 130.99) | (109.24, 121.80) | (156.62, 201.23) |

TABLE IIb

| Metaxalone | AUC(last) | AUCinf | Cmax | Tmax | T1/2 |
|---|---|---|---|---|---|
| Treatment A Least Squares Mean | 8439.62 | 8541.31 | 1773.61 | 4.29 | 2.37 |
| Treatment B Least Squares Mean | 6961.81 | 7478.90 | 983.37 | 3.32 | 9.04 |

With a 5% significance level, the ANOVA detected statistically significant differences between treatments for ln-transformed AUC(last), AUCinf, and Cmax, as well as for untransformed AUC(last), AUC(inf), Cmax, Tmax, T½, and Kel. The ANOVA detected no statistically significant differences between periods or between sequences.

The mean $T_{1/2}$ (half-life) of metaxalone with food and without food were 2.37 and 9.04 hours respectively. The exact reason for this discrepancy is unclear. However, the AUC last is outside the confidence interval, indicating a significant food effect.

Ratio (A/B) of least-squares means for AUC(last), AUC (inf) and Cmax were 123.48%, 115.35% and 177.53%, respectively demonstrating that metaxalone administered with food increased both its rate and extent of absorption.

ANOVA detected statistically significant differences between treatments for ln-transformed AUC(last), AUC (inf), and Cmax, as well as for untransformed AUC(last), AUC(inf),Cmax, T½, and Kel. ANOVA did not detect any statistically significant differences between treatments for untransformed Tmax.

Conclusion: Administration with food increases both the rate and extent of absorption of metaxalone 400 mg tablets when administered as a single dose. The bioavailability of metaxalone 400 mg tablets increased when administrated with food.

Article of Manufacture

The article of manufacture comprises a container holding an immediate release pharmaceutical composition suitable for oral administration of metaxalone in combination with printed labeling instructions providing a discussion of when a particular dosage form should be administered with food and when it should be taken on an empty stomach. The composition will be contained in any suitable container capable of holding and dispensing the dosage form and which will not significantly interact with the composition and will further be in physical relation with the appropriate labeling advising that an immediate release tablet dosage form has less somnolence associated with its use if taken on an empty stomach and an immediate release multiparticulate dosage form has less somnolence associated with its use if taken with food. The labeling instructions will be consistent with the methods of treatment as described hereinbefore.

The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

While the invention has been described by discussion of embodiments of the invention and non-limiting examples thereof, one of ordinary skill in the art may, upon reading the specification and claims, envision other embodiments and variations which are also within the intended scope of the invention and therefore the scope of the invention shall only be construed and defined by the scope of the appended claims.

We claim:

1. A method of increasing the oral bioavailability of metaxalone to a patient receiving metaxalone therapy comprising administering to the patient a therapeutically effective amount of metaxalone in a pharmaceutical composition with food.

2. The method of claim 1 wherein the therapeutically effective amount is 200 mg to 900 mg.

3. The method of claim 1 wherein the therapeutically effective amount is 400 mg to 800 mg.

4. The method of claim 1 wherein the administration to the patient occurs between 30 minutes prior to 2 hours after consuming food.

5. The method of claim 1 wherein the administration to the patient is substantially at the same time as the consumption of the food.

6. The method of claim 1 wherein the administration to the patient is immediately after the consumption of food up to 1 hour after said consumption.

7. The method of claim 1 wherein the pharmaceutical composition comprises a tablet.

8. The method of claim 7 wherein the tablet is in unit dosage form.

9. A method of increasing the rate and extent of absorption of an oral dosage form of metaxalone as measured by the drug concentration attained in the blood stream over time in a patient in need of a therapeutic effect thereof comprising, administering to the patient a therapeutically effective amount of metaxalone in a pharmaceutical composition with food.

10. The method of claim 9 wherein the therapeutically effective amount is about 200 mg to about 900 mg.

11. The method of claim 9 wherein the therapeutically effective amount is from about 400 mg to about 800 mg.

12. The method of claim 9 wherein the administration to the patient occurs between about 30 minutes prior to about 2 hours after consuming food.

13. The method of claim 9 wherein the administration to the patient is substantially at the same time as the consumption of the food.

14. The method of claim 9 wherein the administration to the patient is immediately after the consumption of food up to about one hour after said consumption.

15. The method of claim 9 wherein the pharmaceutical composition comprises a tablet.

16. The method of claim 15 wherein the pharmaceutical composition comprises a unit dosage form.

17. A method of increasing the oral bioavailability of metaxalone to a patient receiving metaxalone therapy comprising administering to the patient a pharmaceutical tablet comprising 400 mg to 800 mg of metaxalone, with food, wherein the administration results in an increase in the maximal plasma concentration (Cmax) and extent of absorption (AUC(last)) of metaxalone compared to administration without food.

18. The method of claim 17 wherein the administration to the patient occurs between 30 minutes prior to 2 hours after consuming food.

19. The method of claim 17 wherein the administration to the patient is substantially at the same time as the consumption of the food.

20. The method of claim 17 wherein the administration to the patient is immediately after the consumption of food up to 1 hour after said consumption.

21. The method of claim 1, further comprising informing the patient that the administration of a therapeutically effective amount of metaxalone in a pharmaceutical composition with food results in an increase in the maximal plasma concentration (Cmax) and extent of absorption (AUC(last)) of metaxalone compared to administration without food.

22. The method of claim 1, wherein the metaxalone is from a container with printed labeling advising that administration with food results in an increase in the maximal plasma concentration (Cmax) and extent of absorption (AUC(last)) of metaxalone compared to administration without food.

* * * * *

UNITED STATES PATENT AND TRADEMARK OFFICE
CERTIFICATE OF CORRECTION

PATENT NO.   : 6,407,128 B1
DATED        : June 18, 2002
INVENTOR(S)  : Scaife et al.

It is certified that error appears in the above-identified patent and that said Letters Patent is hereby corrected as shown below:

Column 1,
Line 38, before "Nov." insert open parenthesis -- (Nov. --;

Column 2,
Line 67, "th e" should read -- the --;

Column 5,
Line 29, "in-transformed" should read -- 1n-transformed --,
Line 66, "in-transformed" should read -- 1n-transformed --; and Column 6,
Line 40, "In-transformed" should read -- 1n-transformed --.

Signed and Sealed this

Twenty-third Day of July, 2002

Attest:

Attesting Officer

JAMES E. ROGAN
*Director of the United States Patent and Trademark Office*